United States Patent
Hinton, Jr.

(10) Patent No.: US 7,655,454 B1
(45) Date of Patent: Feb. 2, 2010

(54) **BACTERIOLOGICAL CULTURE MEDIUM FOR *CAMPYLOBACTERIACEAE* SPECIES**

(75) Inventor: Arthur Hinton, Jr., Athens, GA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 184 days.

(21) Appl. No.: 11/077,107

(22) Filed: Mar. 9, 2005

(51) Int. Cl.
*C12N 1/20* (2006.01)
*C12N 1/00* (2006.01)

(52) U.S. Cl. .................................. 435/253.6; 435/243

(58) Field of Classification Search ............... 435/253.6
See application file for complete search history.

(56) References Cited

U.S. PATENT DOCUMENTS

| | | | | |
|---|---|---|---|---|
| 5,302,388 | A * | 4/1994 | Doyle et al. | 424/93.3 |
| 5,498,528 | A | 3/1996 | King | |
| 5,849,289 | A * | 12/1998 | Dobrogosz et al. | 424/93.45 |
| 5,866,375 | A | 2/1999 | Figura et al. | |
| 5,891,709 | A | 4/1999 | Stern et al. | |
| 5,902,742 | A | 5/1999 | Petter et al. | |
| 6,368,847 | B1 * | 4/2002 | Line et al. | 435/253.6 |
| 6,670,184 | B2 * | 12/2003 | Chiarello et al. | 435/404 |

OTHER PUBLICATIONS

European Patent Application No. 95939410.7, International No. PCT/JP95/02531, Ikeda et al., Aug. 12, 1995.
Queiroz, Dulciene M. et al., "Indicator Medium for Isolation of *Campylobacter pylori*," *Journal of Clinical Microbiology*, Dec. 1987, vol. 25, No. 12, pp. 2378-2379.
Atlas, Ronald M., *Handbook of Microbiological Media*, pp. 179-190.
Bolton, F.J. et al., "*Campylobacter* Biotyping Scheme of Epidemiological Value," *J Clin. Pathol.*, 1984, vol. 37, pp. 677-681.
Bolton, F.J. et al., "Development of a Blood-free *Campylobacter* Medium: Screening Tests on Basal Media and Supplements, and the Ability of Selected Supplements to Facilitate Aerotolerance," *The Society for Applied Bacteriology*, 1983, pp. 115-125.
University of Georgia, "*Acrobacter butzleri*," *UGA Center for Food Safety*, Research Programs, pp. 1-2.
Bolton, F.J., et al., "Blood-Free Selective Medium for Isolation of *Campylobacter jejuni* from Feces," *Journal of Clinical* Microbiology, Feb. 1984, vol. 19, No. 2, pp. 169-171.
Chaveerach, P. et al., "Survival and Resuscitation of Ten Strains of *Campylobacter jejuni* and *Campylobacter coli* Under Acid Conditions," Applied and Envir. Micr., Jan. 2003, vol. 69, No. 1, pp. 711-714.

* cited by examiner

*Primary Examiner*—Vera Afremova
(74) *Attorney, Agent, or Firm*—John D. Fado; Gail E. Poulos

(57) ABSTRACT

A chemically defined media supplemented with organic acids is used for supporting in vitro growth of *Campylobacter* and *Arcobacter* species.

1 Claim, 1 Drawing Sheet

BACTERIOLOGICAL CULTURE MEDIUM FOR *CAMPYLOBACTERIACEAE* SPECIES

BACKGROUND OF THE INVENTION

1. Field of the Invention

This invention relates to a chemically defined media supplemented with organic acids that support in vitro growth of *Campylobacter* and *Arcobacter* bacteria and to methods for using the media to culture microorganisms of the genera *Campylobacter* and *Arcobacter*.

2. Description of the Related Art

Industrial scale culture of *Campylobacter* and *Arcobacter* is important for the production of relevant amounts of the same microorganisms and for products produced by these microorganisms during fermentation.

*Campylobacter* species have been recognized as important causative agents of foodborne illness. There is a strong association of foods of animal origin in the transmission of disease to humans. Contaminated water, milk, poultry, and red meats have been identified as vectors of the enteropathogen (Hanninen, Acta Vet. Scand., Volume 23, 88-98, 1982; Ooserom et al., J. Food Prot., Volume 46, 339-344, 1983). Other reservoirs of *Campylobacter* include asymptomatic human carriers, pets such as cats and dogs, and rodents. *Campylobacter jejuni, Campylobacter coli* and *Campylobacter lari* are known to cause an estimated 2.2 million cases of foodborne gastroenteritis per year in the United States alone (Tauxe et al., American J. Public Health, Volume 77, 1219-1221, 1987). The vast majority of these cases are associated with the consumption of improperly prepared or handled foods. *C. jejuni* and *C. coli* are the 2 major species of the genus and are responsible for about 95% of human cases of campylobacteriosis. *C. jejuni* is the most notable species and over 60 different serotypes of this bacterium have been identified (Franco, J. Food Prot., Volume 51, 145-153, 1988). Although the origin of this disease in humans is primarily linked to poultry, the food microbiology and poultry communities have been slow in directing substantive attention toward formulating defined media that support the growth of the bacteria. This has been due, in part, to the unique physiological requirements of these organisms, which require specialized equipment and conditions for their isolation and culture from foods and clinical specimens. *Campylobacter* require special microaerobic atmospheres and nutritionally rich media for growth (Kiggin et al, J. Bacteriology, Volume 72, 397-400, 1956.)

*Campylobacter* and *Arcobacter* belong to the bacterial family Campylobacteriaceae. All Campylobacteriaceae exhibit similar phenotypic characteristics and they are fastidious with exacting nutritional requirements (Park, Int. Food Microbiol., Volume 74, 177-188, 2002). The bacteria do not metabolize carbohydrates but they may obtain energy by oxidizing amino acids and intermediates of the tricarboxylic acid cycle (TCA) (Stern and Line, *Campylobacter*, In Lund et al. (eds), The Microbiological Safety and Quality of Food, Aspen Publishers, Gaithersburg, Md., Volume II, 1040-1056, 2000). Although Campylobacteriaceae can grow on non-supplemented media that is currently available, their growth is enhanced by the addition of supplements to these media. Existing media for the culture of *Campylobacter* and *Arcobacter* species are often supplemented with undefined components such as blood, serum red cells, etc. which do not allow for exact conditions in experimental and production fermentation. Defibrinated or lysed blood is a common supplement used in *Campylobacter* media; however blood-free media are desirable because of the cost and variability of the quality of animal blood used to supplement the media (Bolton et al., J. of Clin. Microbiol., Volume 19, 169-171, 1984). Many of the media used to culture Campylobacteriaceae also contain oxygen scavengers such as, charcoal, ferrous sulphate, sodium metabisulphite, sodium pyruvate, or hemin that protect bacteria from the toxic effects of oxygen derivatives (Corry et al., Int. J. Food Microbiol., Volume 26, 43-76, 1995; George et al., J. Clin. Microbiol., Volume 8, 36-41, 1978; Line, J. Food Prot., Volume 64, 1711-1715, 2001). These supplements may be used in various combinations with or without blood.

Therefore, there is a need in the art for a chemically defined, blood-free media that supports the growth of *Campylobacter* and *Arcobacter* and allows for the maintenance of these bacterial cultures. The present invention, described below, is to improved media that is chemically defined, blood-free, and different from related art media.

SUMMARY OF THE INVENTION

It is therefore an object of the present invention to provide improved chemically defined media for the culture *Campylobacter* and *Arcobacter* species.

Another object of the present invention is to provide chemically defined media for the culture of *Campylobacter* and *Arcobacter* species, which includes at least one organic acid.

A still further object of the present invention is to provide chemically defined media for the culture of *Campylobacter* and *Arcobacter* species which includes organic acids selected from the group consisting of citric, fumaric acid, DL-lactic acid, DL-malic acid, succinic acid, and mixtures thereof.

Another object of the present invention is to provide a method for culturing species of Campylobacteriaceae including culturing the species in a chemically defined media that includes at least one organic acid.

A still further object of the present invention is to provide a method for culturing species of Campylobacteriaceae including culturing the species in a chemically defined media that includes an amino acid source in amounts to at least increase the growth of Campylobacteriaceae species in culture, a vitamin source in amounts to at least increase the growth of Campylobacteriaceae species in culture, at least one organic acid in amounts to at least increase the growth of Campylobacteriaceae species in culture, and an oxygen scavenger in amounts to at least increase the growth of Campylobacteriaceae species in culture.

A still further object of the present invention is to provide a method for culturing species of Campylobacteriaceae including culturing the species in a chemically defined media that includes at least one organic acid selected from citric acid, DL-lactic acid, DL-malic acid, fumaric acid, succinic acids or mixtures thereof in amounts to at least increase the growth of Campylobacteriaceae species in culture.

A still further object of the present invention is to provide a method for culturing Campylobacteriaceae species including culturing the species in a chemically defined media that includes at least one organic acid in a concentration of between about 10 mM and about 40 mM.

Further objects and advantages of the present invention will become apparent from the following description.

DETAILED DESCRIPTION OF THE INVENTION

Figure 1:
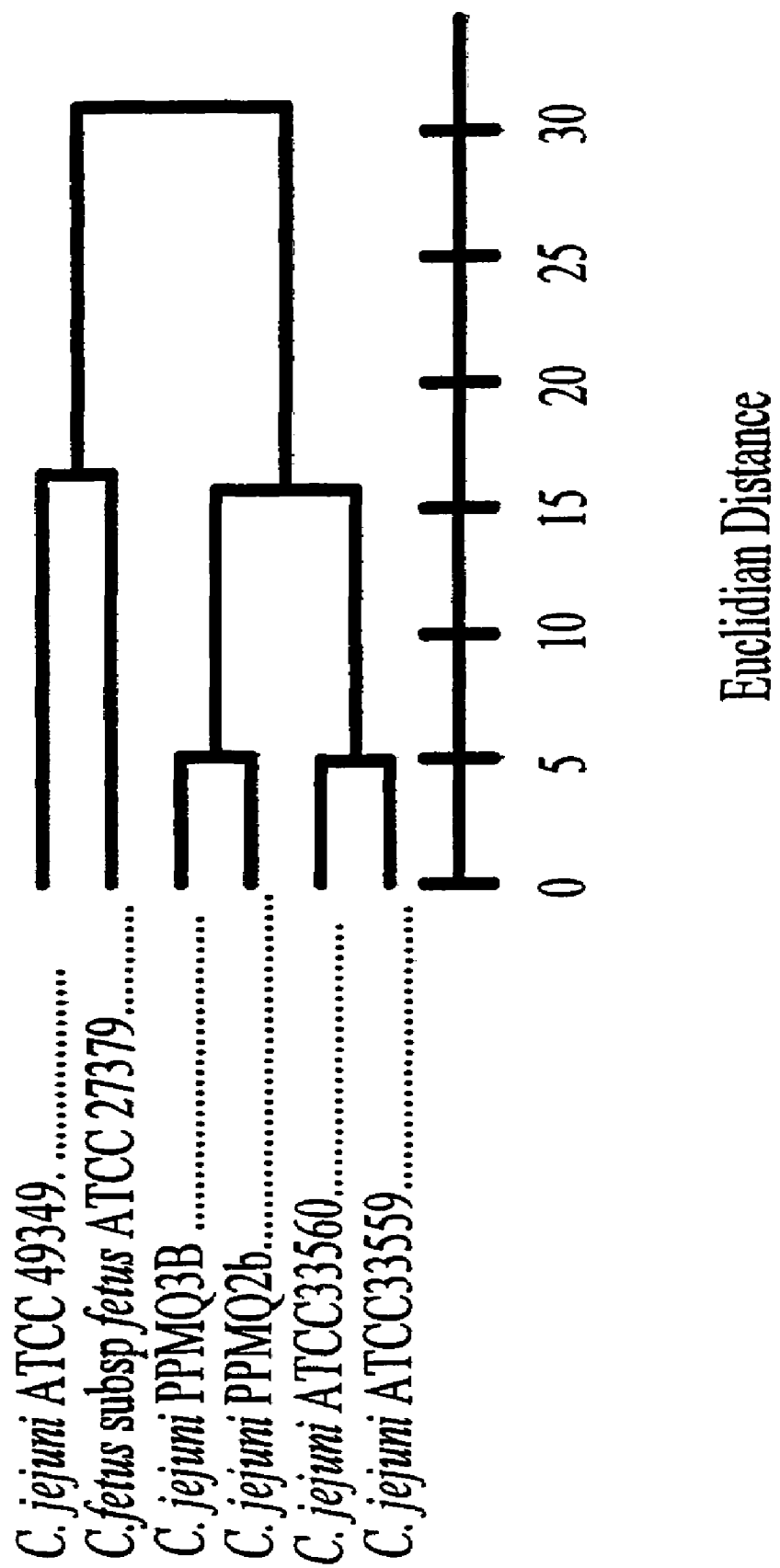
FIG. 1 is a drawing of a MIDI Sherlock Microbial Identification System dendrogram of *Campylobacter* species.

*Campylobacter* are fastidious bacteria and are very sensitive to environmental stress (Herbert et al., J. Clin. Microbiol., Volume 15, 1065-1073, 1982; Kaplan, *Campylobacter*. In Manual of Clincal Microbiology, Third Edition, American Society for Microbiology, Washington D.C., 1980; Park, Int. J. Food Microbiol., Volume 74, 177-188, 2002). Many of the media used to culture *Campylobacter* include blood or hematin as nutritional supplements (Corry et al., Int. J. Food Microbiol., Volume 26, 43-76, 1995; Line, J. Food Prot., Volume 64, 1711-1715, 2001; Mihowich et al., Food Microbiol., Volume 15, 119-125, 1998; Rosef, Acta. Vet. Scand, Volume 22, 149-151, 1981; Stern et al., J. Food Prot., Volume 55, 663-666, 1992). The bacteria are microaerophiles that grow best in an atmosphere containing about 5-10% oxygen (Franco, J. Food Prot., Volume 51, 145-153, 1988; George et al., J. Clin. Microbiol., Volume 8, 36-41, 1978). Thermophilic species of *Campylobacter* grow well at about 42° C., but all strains of the genus grow well at about 37° C. (Shane, Rev. Sci. Tech., Volume 19(2), 376-395, 2000).

The media of this invention may be used for the culture of *Campylobacter* and *Arcobacter* species such as, for example, *C. jejuni, C. coli, C. fetus, A. butzleri*, etc., from a variety of sources. The culture media of the present invention may be prepared using techniques conventional in the art. The basal medium components include an amino acid source, a vitamin source, an energy source, and an oxygen scavenger. Agar may be added as a solidifying agent. The components are mixed, heated to boiling and sterilized by autoclaving. Organic acid mixtures are sterilized separately from components of the basal media. After cooling the sterilized medium to about 50° C.-55° C., filter-sterilized supplements are added with mixing, and the medium finally poured into a culture container, such as a petri dish, for example, and cooled to allow the agar to solidify, if necessary.

In one embodiment of the present invention, the improvement includes the addition of organic acids to media in concentrations that at least increase the growth of the *Campylobacter* or *Arcobacter* species as compared to growth on media without organic acids while not significantly inhibiting the growth of these species. Any nutrient medium and energy source effective to support growth of *Campylobacter* species may be used. Suitable amino acid sources include, for example, but are not limited to peptone, tryptone, Tryptose, soytone, yeast extract, and beef extract (Difco). In the preferred embodiments of the present invention, proteose peptone #3 and yeast extract (Difco) are the preferred amino acid sources.

The vitamin source in the media of the present invention includes yeast extract.

To enhance aerotolerance of the microorganisms, oxygen scavengers are added to the media of the present invention and include but are not limited to hemin, L-cysteine hydrochloride monohydrate, thioglycolate, sodium bisulfite, sodium metabisulfite, etc.

Organic acids, an energy source, are added to the medium to enhance bacterial growth and include, for example, citric acid, DL-lactic acid, DL-malic acid, fumaric acid, and succinic acid. The amount of organic acid added to the media of the present invention should be an amount to at least increase the growth of a Campylobacteriaceae species in culture over that which is seen in species grown in cultures with media that contain undefined components such as blood, serum, red cells, etc, for example.

The concentration and amount of each of the components of the media of the present invention should be an amount to at least increase the growth of a Campylobacteriaceae species in the chemically defined culture of the present invention over that which is seen in species grown in cultures with related art media that contain undefined components such as blood, serum, red cells, etc. The amount of each component of the basal or nutrient media should be effective to promote growth of Campylobacteriaceae species, but should not inhibit the growth of the bacteria. Without being limited thereto, preferred ranges for each of the components of the defined media of the present invention include: amino acid sources including proteose peptone #3 from about 0.5% to about 2.0%, vitamin source such as yeast extract from about 0.5% to about 2.0%, and organic acids from about 10 to about 40 mM each. The final pH of the media must be adjusted to from about pH 7.0 to about pH 7.5.

The following examples illustrate the use of the invention. They are intended to further illustrate the invention and are not intended to limit the scope of the invention as defined by the claims.

EXAMPLE 1

Six *Campylobacter* isolates were used in the following examples. Four of the *Campylobacter* isolates were obtained from the American Type Culture Collection (ATCC, Manassas, Va. 20110) and were ATTC strain *C. fetus* susp. *fetus* ATCC 27374, *C. coli* ATCC 33559, *C. jejuni* subsp. *jejuni* ATCC 33560, and *C. jejuni* subsp. *doylei* ATCC 49349. The other two isolates, *C. jejuni* PPMQ2b and *C. jejuni* PPMQ3b, were obtained from rinsates of whole carcass rinses (WCR) of processed broiler carcasses taken from a local poultry processing facility. Whole carcass rinses were conducted by shaking broiler carcasses in about 100 ml of about 0.1% Bacto Peptone (Difco Laboratories, Detroit, Mich. 48232) solution in plastic bags for approximately 1 minute. Rinsates were decanted and serial dilutions of rinsates were plated on *Campylobacter* Agar prepared from the Bacto *Campylobacter* Agar Kit Blaser (Difco). Inoculated plates were incubated in a BBL GasPak Jar (Becton Dickinson Microbiology Systems, Sparks, Md. 21152) with an activated CampyPak Plus Hydrogen+$CO_2$ with Intergral Palladium Catalyst (Becton Dickinson Microbioly Systems) for about 48 hours at about 42° C. *Campylobacter*-like colonies were removed from the incubated plates and presumptively identified using the Latex-Campy (jcl)™Campylobacter Culture Confirmation Test (PanBio, Inc., Baltimore, Md. 21227). The poultry isolates that were positive from the latex agglutination test were identified with the MIDI Sherlock Microbial Identification System (MIS)(MIDI, Inc., Newark, Del. 19713). Stock cultures of all isolates were maintained by transferring the bacteria to Blood Agar (Remel, Lenexa, Kans. 66215) and incubating in a BBL GasPak with a CampyPak Plus Hydrogen+$CO_2$ with Integral Palladium Catalyst for about 48 hours at about 37° C. New stock cultures were grown at about 1-2 week intervals and stored at about 4° C.

The dendrogram program of the MIDI Sherlock MIS (MIDI Development and Support Team, Dendrogram, Sherlock Library Generation System, Version 4.0, MIDI, Inc., Newark Del., 2001) was used to determine the degree of relatedness of the isolates. Isolates linked at a Euclidean Distance (ED) of $\leq 6.0$ are considered to belong to the same subspecies and isolates linked at an ED of $\leq 2.5$ are considered to belong to the same strain.

*C. fetus* subsp. *fetus* ATCC 27374 and *C. jejuni* subsp. *doylei* ATCC 49349 were linked at a ED of approximately 16. The MIDI Sherlock MIS identified *C. coli* ATCC 33559 as *C. jejuni* and linked this isolate at an ED of approximately 5 with C. jejuni subsp. jejuni ATCC 33560. This finding indicated that the MIDI system considered these isolates to be the same subspecies of Campylobacter jejuni. The MIDI dendrogram indicated that the two poultry isolates, C. jejuni PPMQ2b and C. jejuni PPMQ3b were also linked at the subspecies level and that they were more closely related to C. coli ATCC 33559 and C. jejuni subsp. jejuni ATCC 33560 than to C. fetus subsp. fetus ATCC 27374 or C. jejuni subsp. doylei ATCC 49349.

EXAMPLE 2

Stock cultures of Campylobacter spp., as described above in Example 1, were tested with individual organic acids and with mixtures of organic acids. The stock cultures were streaked onto Blood agar plates and incubated in a BBL GasPak Jar with a CampyPak Plus Hydrogen+$CO_2$ with Integral Palladium Catalyst for about 48 hours at about 37° C. After incubation, cultures were harvested by adding about 9 ml of approximately 0.1% Bacto Peptone solution to the surface of the plates and using sterile bacterial cell spreaders to scrape cell growth from the plates. Harvested bacterial suspensions for each of the isolates contained approximately $10^8$ colony forming units (cfu)/ml. Approximately 0.1 ml of the bacterial suspension was added to about 10 ml of broth media. The media contained individual organic acids or mixtures of organic acids. Solutions of Citric (Mallinckrodt, Paris, Ky. 40361), fumaric (Sigma Chemical Com., St. Louis, Mo. 63178), DL-lactic acid (Sigma), DL-Malic acid (Sigma) and succinic acid (Sigma) of the appropriate molarity were prepared in distilled water. The pH of the acid solutions was adjusted to about pH 7.0 with sodium hydroxide (Mallinkrodt), and the solutions were sterilized by autoclaving at about 121° C. for approximately 15 minutes. The appropriate acid solution was added to a sterile basal medium composed of tryptose (Difco), yeast extract (Difco), and L-cysteine hydrochloride monohydrate (Sigma). The basal medium was supplemented with organic acids to produce a final medium of tryptose approximately 10 g/liter, yeast extract approximately 5 g/liter, L-cysteine hydrochloride monohydrate approximately 0.4 g/liter, and either approximately 0, 10, 20, 30, 40, or 50 mM of either citric, fumaric, lactic, malic, or succinic acid. For mixtures of acids, the basal medium was supplemented with equimolar concentrations of fumaric, malic, lactic, and succinic acids. The acids were added to the media to produce a final concentration of approximately 10, 20, 30, 40, or 50 mM of each of the acids in the media.

The test tubes containing the inoculated media were transferred to a Coy Anaerobic Chamber (Coy Laboratory Products, Inc., Grass Lake Mich. 49240), and 0.1 ml of contents of the tubes were pipetted into wells of a Honeycomb 2 cuvette plate (Labsystems, Inc., Franklin, Mass. 02038). Cell suspensions in the wells were overlaid with approximately 0.1 ml of sterilized, heavy, white mineral oil (Sigma). The filled Honeycomb 2 plates were then removed from the anaerobe chamber and placed in the incubator tray of a Bioscreen C Microbiology Reader (Labsystems). Labsystems BioLink PC software (Labsystems) was used to program the Bioscreen to incubate the cultures at about 37° C. for about 24 hours. The Bioscreen measured culture optical density (OD) at approximately 10 minute intervals with the wide band (420-580 nm) filter immediately after about 10 seconds of medium intensity shaking of the cultures. Each experiment was replicated 5 times.

For statistical analysis, group means of culture OD were compared to determine significant differences in the turbidity of bacterial cultures grown in different media. Data were analyzed using GraphPad InStat version 3.0 for Windows 95 (GraphPad Software, San Diego, Calif. 92121) to perform One-Way Analysis of Variance (ANOVA). When ANOVA detected significant differences in group means, the Tukey-Kramer test was used to determine significant differences in group means. All significant differences were determined at $P<0.05$.

Growth of all cultures of Campylobacter spp. was influenced by the type and concentration of organic acid used to supplement the basal media inoculated with the bacteria. Although the bacteria varied in the types and concentrations of acids that stimulated their growth, the isolates that were linked the closest by the MIDI Sherlock dendrogram usually exhibited the most similarity in their growth patterns in the supplemented media.

Although C. fetus subsp. fetus ATCC 27374 and C. jejuni subsp. doylei ATCC 49349 were linked at an ED of approximately 16 (FIG. 1), these isolates still exhibited some similarities in growth in media supplemented with organic acids (Tables 1 and 2). The OD of C. fetus subsp. fetus ATCC 27374 cultures grown in media supplemented with approximately 10, 20, 30, 40, or 50 mM of fumaric, malic or succinic acid was significantly higher than the OD of cultures in non-supplemented media. Similarly, the absorbance of cultures of C. jejuni subsp. doylei ATCC 49349 grown in media supplemented with approximately 20, 30, 40 and 50 mM of fumaric, malic, or succinic acid was significantly higher than the absorbance of isolates grown in the control media. However, when these cultures were grown in media supplemented with approximately 50 mM lactic acid, the absorbance of the resultant cultures was not significantly different than the absorbance of cultures grown in non-supplemented media. Additionally, the absorbance of cultures of C. fetus subsp. fetus ATCC 27374 grown in media containing approximately 50 mM malic acid was significantly lower than the absorbance of cultures grown in media supplemented with approximately 40 mM malic aid. The decreased absorbance of cultures grown in media supplemented with increased concentrations of lactic and malic acid indicated that higher concentrations of these acids could inhibit the growth of the isolate at about pH 7.0. Organic acids are effective food preservatives because they act as acidulants that lower the pH to levels that reduce bacterial growth (Dziezak, Food Tech., Volume 44(1), 78-83, 1990). Poultry carcass washes containing lactic acid (Yogasundram et al., Vet. Res. Commun., Volume 11, 1-40, 1987) and succinic acid (Cox et al., J. Food Sci., Volume 39, 985-987, 1974) have been examined as treatments for reducing microbial contamination of processed poultry. Concentrations of organic acid used to supplement basal media in this study generally exhibit antimicrobial activity towards most bacteria. Adjusting the pH of the media used in the present study to pH about 7.0 diminished the inhibitory activity of the acids and allowed the Campylobacter to grow in these concentrations of the organic acids. Neither C. fetus subsp. fetus ATCC 27374 nor C. jejuni subsp. doylei ATCC 49349 cultures exhibited significant increased absorbances when grown in media supplemented with approximately 10, 20, 30, 40, or 50 mM of citric acid. The inability of citric acid to stimulate Campylobacter growth at any level of supplementation indicated either that the bacteria could not utilize the organic acid or that citric acid inhibited the growth of the bacteria at all levels.

The MIDI Sherlock MIS identified C. coli ATCC 33559 as C. jejuni and linked this isolate at an ED of approximately 5 with C. jejuni subsp. jejuni ATCC 33560 (FIG. 1). This finding indicated that the MIDI system considered these isolates to be the same subspecies of Campylobacter jejuni. These were the only two isolates that exhibited significantly more growth in media supplemented with approximately 30 or 40 mM of citric acid (Tables 3 and 4). The absorbance of cultures grown in media supplemented with approximately 50 mM citric acid was not significantly different from the absorbance of isolates grown in non-supplemented media. The absorbance of cultures of *C. coli* ATCC 33559 cultures grown in media supplemented with approximately 30, 40, or 50 mM lactic acid was significantly greater than the OD of cultures in non-supplemented media, while the growth of *C. jejuni* subsp. *jejuni* ATCC 33560 cultures in media supplemented with approximately 20, 30, 40, or 50 mM lactic acid was significantly higher than the OD of cultures grown in non-supplemented media. The absorbance of cultures of *C. coli* ATCC 3359 and *C. jejuni* subsp. *jejuni* ATCC 33560 grown in media supplemented with approximately 20, 30, 40, and 50 mM of fumaric or malic acid and in approximately 30, 40, or 50 mM succinic acid was significantly higher than the growth of cultures grown in non-supplemented media.

The MIDI dendrogram (FIG. 1) indicated that the two poultry isolates, *C. jejuni* PPMQ2b and *C. jejuni* PPMQ3b, were also linked at the subspecies level and that they were more closely related to *C. coli* ATCC 27374 or *C. jejuni* subspp. *doylei* ATCC 49349. Even though *C. jejuni* PPMQ2b and *C. jejuni* PPMQ3b were closely related, they exhibited many differences in their growth patterns in media supplemented with organic acids (Tables 5 and 6). *C. jejuni* PPMQ3b cultures grown in media supplemented with approximately 20 mM citric acid exhibited a small but significantly higher absorbance than cultures grown in non-supplemented media. The absorbance of cultures of *C. jejuni* PPMQ2b grown in media supplemented with citric acid was not significantly different from the absorbance of cultures grown in non-supplemented media. *C. jejuni* PPMQ3b also exhibited greater sensitivity to lactic acid than *C. jejuni* PPMQ2b as only cultures grown in media supplemented with 20 mM lactic acid had an absorbance that was significantly greater than the OD of cultures grown in non-supplemented media.

Cultures of *C. jejuni* PPMQ2b grown in media supplemented with approximately 20, 30, 40, or 50 mM lactic acid had absorbances that were significantly greater than the ODs of cultures grown in non-supplemented media. The absorbance of *C. jejuni* PPMQ3b cultures were significantly higher when grown in media supplemented with approximately 20 mM fumaric acid than when grown in non-supplemented media. Supplementing media with approximately 30 mM of fumaric acid was required to produce *C. jejuni* PPMQ2b cultures with a higher absorbance than cultures grown in non-supplemented media. *C. jejuni* PPMQ3b also required less malic acid (approximately 20 mM) than *C. jejuni* PPMQ2b (approximately 40 mM) to produce cultures with significantly higher absorbances than cultures grown in non-supplemented media. *C. jejuni* PPMQ3b was able to utilize approximately 40 and 50 mM of succinic acid to produce cultures with significantly higher absorbances than cultures grown in non-supplemented media. In contrast, none of the concentrations of succinic acid produced significantly higher absorbances in cultures of *C. jejuni* PPMQ2b over that of non-supplemented media.

Mixtures of equimolar concentrations of fumaric, lactic, malic, and succinic acids stimulated the growth of all the *Campylobacter* isolates (Table 7). Except for the *C. jejuni* PPMQ2b isolate, the absorbance of each *Campylobacter* culture was significantly higher in media supplemented with a mixture containing approximately 10, 20, 30, or 40 mM of each organic acid than in non-supplemented media. The absorbance of all isolates grown in media supplemented with approximately 50 mM of each acid was not significantly different from the absorbance of cultures of the isolate grown in non-supplemented media. Additionally, the absorbance of cultures of *C. jejuni* PPMQ2b grown in media supplemented with approximately 40 mM of each acid was not significantly different from the absorbance of cultures grown in non-supplemented media. The inability of cultures to grow in media supplemented with higher concentrations of acid mixtures again illustrated that some concentrations of organic acids can inhibit *Campylobacter* growth even when the pH of the media had been adjusted to approximately pH 7.0.

TABLE 1

Optical Density[1] of *Campylobacter fetus* subsp. *fetus* ATCC 27374 cultures grown at 37° C. for about 48 hours in broth media supplemented with various concentrations of organic acids.

| Acid Supplement | Acid Concentration (mM) | | | | | |
|---|---|---|---|---|---|---|
| | 0 | 10 | 20 | 30 | 40 | 50 |
| None | $0.15^{a,w} \pm 0.04$ | $0.15^{a,w} \pm 0.04$ | $0.15^{a,w} \pm 0.04$ | $0.15^{a,w} \pm 0.04$ | $0.15^{a,w} \pm 0.04$ | $0.15^{a,w} \pm 0.04$ |
| Citric | $0.15^{a,w} \pm 0.04$ | $0.11^{a,w} \pm 0.00$ | $0.14^{a,w} \pm 0.05$ | $0.14^{a,w} \pm 0.03$ | $0.14^{a,w} \pm 0.03$ | $0.12^{a,w} \pm 0.01$ |
| Fumaric | $0.15^{a,w} \pm 0.04$ | $0.36^{b,y} \pm 0.04$ | $0.47^{c,z} \pm 0.04$ | $0.46^{c,y} \pm 0.02$ | $0.42^{bc,x} \pm 0.04$ | $0.42^{bc,y} \pm 0.05$ |
| Lactic | $0.15^{a,w} \pm 0.04$ | $0.26^{ab,x} \pm 0.07$ | $0.37^{bc,y} \pm 0.02$ | $0.36^{bc,x} \pm 0.06$ | $0.38^{c,x} \pm 0.03$ | $0.23^{a,x} \pm 0.09$ |
| Malic | $0.15^{a,w} \pm 0.04$ | $0.30^{b,xy} \pm 0.01$ | $0.35^{bc,xy} \pm 0.02$ | $0.37^{c,xy} \pm 0.04$ | $0.37^{c,x} \pm 0.06$ | $0.34^{b,y} \pm 0.02$ |
| Succinic | $0.15^{a,w} \pm 0.04$ | $0.27^{b,x} \pm 0.01$ | $0.30^{bc,x} \pm 0.04$ | $0.36^{cd,x} \pm 0.06$ | $0.40^{d,x} \pm 0.04$ | $0.41^{d,y} \pm 0.06$ |

[1]Values are averages ± standard deviation. n = 5.
$^{a-d}$Different superscripts indicate significant differences in the absorbance of cultures supplemented with different concentrations of the same acid.
$^{w-z}$Different superscripts indicate significant differences in the absorbance of cultures supplemented with the same concentration of different acids.

TABLE 2

Optical Density of *Campylobacter jejuni* subsp. *doylei* ATCC 49349 cultures grown at about 37° C. for about 48 hours in broth meida supplemented with various concentrations of organic acids.

| Intermediate | Intermediate Concentration (mM) | | | | | |
|---|---|---|---|---|---|---|
| | 0 | 10 | 20 | 30 | 40 | 50 |
| None | $0.15^{a,w} \pm 0.01$ | $0.15^{a,w} \pm 0.01$ | $0.15^{a,w} \pm 0.01$ | $0.15^{a,w} \pm 0.01$ | $0.15^{a,w} \pm 0.01$ | $0.15^{a,w} \pm 0.01$ |
| Citric | $0.15^{a,w} \pm 0.01$ | $0.13^{a,w} \pm 0.01$ | $0.13^{a,w} \pm 0.00$ | $0.14^{a,w} \pm 0.03$ | $0.13^{a,w} \pm 0.01$ | $0.12^{a,w} \pm 0.00$ |
| Fumaric | $0.15^{a,w} \pm 0.01$ | $0.14^{a,w} \pm 0.02$ | $0.28^{b,x} \pm 0.06$ | $0.36^{c,x} \pm 0.02$ | $0.37^{c,y} \pm 0.01$ | $0.39^{c,x} \pm 0.04$ |
| Lactic | $0.15^{a,w} \pm 0.01$ | $0.13^{a,w} \pm 0.01$ | $0.24^{c,x} \pm 0.03$ | $0.21^{bc,x} \pm 0.08$ | $0.26^{c,x} \pm 0.05$ | $0.16^{ab,w} \pm 0.02$ |
| Malic | $0.15^{a,w} \pm 0.01$ | $0.15^{a,w} \pm 0.02$ | $0.28^{b,x} \pm 0.01$ | $0.35^{c,x} \pm 0.03$ | $0.36^{c,y} \pm 0.02$ | $0.35^{c,x} \pm 0.02$ |
| Succinic | $0.15^{a,w} \pm 0.01$ | $0.15^{a,w} \pm 0.02$ | $0.23^{b,x} \pm 0.01$ | $0.37^{cd,x} \pm 0.01$ | $0.35^{c,y} \pm 0.03$ | $0.40^{d,x} \pm 0.03$ |

[1]Values are averages ± standard deviation. n = 5.
[a-d]Different superscripts indicate significant differences in the absorbance of cultures supplemented with different concentrations of the same acid.
[w-z]Different superscripts indicate significant differences in the absorbance of cultures supplemented with the same concentration of different acids.

TABLE 3

Optical Density of *Campylobacter coli* ATCC 33559 cultures grown at about 37° C. for about 48 hours in broth media supplemented with various concentrations of organic acids.

| Acid Supplement | Acid Concentration (mM) | | | | | |
|---|---|---|---|---|---|---|
| | 0 | 10 | 20 | 30 | 40 | 50 |
| None | $0.10^{a,w} \pm 0.01$ | $0.10^{a,w} \pm 0.01$ | $0.10^{a,w} \pm 0.01$ | $0.10^{a,w} \pm 0.01$ | $0.10^{a,w} \pm 0.01$ | $0.10^{a,w} \pm 0.01$ |
| Citric | $0.10^{a,w} \pm 0.01$ | $0.10^{a,w} \pm 0.01$ | $0.14^{b,w} \pm 0.01$ | $0.23^{d,wx} \pm 0.01$ | $0.26^{e,x} \pm 0.01$ | $0.16^{c,w} \pm 0.01$ |
| Fumaric | $0.10^{a,w} \pm 0.01$ | $0.14^{a,x} \pm 0.05$ | $0.20^{b,xy} \pm 0.04$ | $0.31^{c,x} \pm 0.05$ | $0.37^{c,x} \pm 0.06$ | $0.35^{c,x} \pm 0.02$ |
| Lactic | $0.10^{a,w} \pm 0.01$ | $0.14^{a,x} \pm 0.02$ | $0.27^{ab,y} \pm 0.06$ | $0.33^{b,x} \pm 0.14$ | $0.33^{b,x} \pm 0.14$ | $0.34^{b,x} \pm 0.11$ |
| Malic | $0.10^{a,w} \pm 0.01$ | $0.17^{a,x} \pm 0.01$ | $0.18^{b,wx} \pm 0.04$ | $0.34^{c,x} \pm 0.08$ | $0.30^{c,x} \pm 0.01$ | $0.33^{c,x} \pm 0.02$ |
| Succinic | $0.10^{a,w} \pm 0.01$ | $0.11^{a,w} \pm 0.01$ | $0.17^{ab,wx} \pm 0.06$ | $0.26^{bc,x} \pm 0.08$ | $0.28^{c,x} \pm 0.06$ | $0.33^{c,x} \pm 0.06$ |

[1]Values are averages ± standard deviation. n = 5.
[a-e]Different superscripts indicate significant differences in the absorbance of cultures supplemented with different concentrations of the same acid.
[w-z]Different superscripts indicate significant differences in the absorbance of cultures supplemented with the same concentration of different acid.

TABLE 4

Optical Density of *Campylobacter jejuni* subsp. *jejuni* ATCC 33560 cultures grown at about 37° C. for about 48 hours in broth media supplemented with various concentrations of organic acids.

| Acid Supplement | Acid Concentration (mM) | | | | | |
|---|---|---|---|---|---|---|
| | 0 | 10 | 20 | 30 | 40 | 50 |
| None | $0.12^{a,w} \pm 0.01$ | $0.12^{a,w} \pm 0.01$ | $0.12^{a,w} \pm 0.01$ | $0.12^{a,w} \pm 0.01$ | $0.12^{a,w} \pm 0.010$ | $0.12^{a,w} \pm 0.01$ |
| Citric | $0.12^{a,w} \pm 0.01$ | $0.12^{a,w} \pm 0.01$ | $0.15^{b,wx} \pm 0.01$ | $0.21^{c,wx} \pm 0.03$ | $0.22^{c,x} \pm 0.02$ | $0.11^{a,w} \pm 0.00$ |
| Fumaric | $0.12^{a,w} \pm 0.01$ | $0.15^{a,w} \pm 0.03$ | $0.18^{b,xy} \pm 0.02$ | $0.27^{c,y} \pm 0.02$ | $0.36^{d,y} \pm 0.01$ | $0.34^{d,x} \pm 0.02$ |
| Lactic | $0.12^{a,w} \pm 0.01$ | $0.11^{a,w} \pm 0.00$ | $0.24^{b,z} \pm 0.05$ | $0.34^{c,y} \pm 0.06$ | $0.34^{c,y} \pm 0.03$ | $0.34^{c,x} \pm 0.06$ |
| Malic | $0.12^{a,w} \pm 0.01$ | $0.14^{a,w} \pm 0.03$ | $0.21^{b,yz} \pm .01$ | $0.3l^{c,y} \pm 0.06$ | $0.32^{c,y} \pm 0.31$ | $0.29^{c,x} \pm 0.05$ |
| Succinic | $0.12^{a,w} \pm 0.01$ | $0.10^{a,w} \pm 0.01$ | $0.17^{a,wxy} \pm 0.03$ | $0.28^{b,y} \pm 0.07$ | $0.29^{b,xy} \pm 0.10$ | $0.28^{b,x} \pm 0.06$ |

[1]Values are averages ± standard deviation. n = 5.
[a-e]Different superscripts indicate significant differences in the absorbance of cultures supplemented with different concentrations of the same acid.
[w-z]Different superscripts indicate significant differences in the absorbance of cultures supplemented with the same concentration of different acids.

TABLE 5

Optical Density[1] of *Campylobacter jejuni* PPMQ2b cultures grown at about 37° C. for about 48 hours in broth media supplemented with various concentrations of organic acids.

| Acid Supplement | Acid Concentration (mM) | | | | | |
|---|---|---|---|---|---|---|
| | 0 | 10 | 20 | 30 | 40 | 50 |
| None | $0.13^{a,w} \pm 0.01$ | $0.13^{a,w} \pm 0.01$ | $0.13^{a,w} \pm 0.01$ | $0.13^{a,w} \pm 0.01$ | $0.13^{a,w} \pm 0.01$ | $0.13^{a,w} \pm 0.01$ |
| Citric | $0.13^{a,w} \pm 0.01$ | $0.12^{a,w} \pm 0.01$ | $0.12^{a,w} \pm 0.01$ | $0.12^{a,w} \pm 0.01$ | $0.13^{a,w} \pm 0.01$ | $0.12^{a,w} \pm 0.00$ |
| Fumaric | $0.13^{a,w} \pm 0.01$ | $0.12^{a,w} \pm 0.01$ | $0.12^{a,w} \pm 0.01$ | $0.35^{b,x} \pm 0.02$ | $0.21^{a,x} \pm 0.10$ | $0.39^{b,x} \pm 0.012$ |

TABLE 5-continued

Optical Density[1] of *Campylobacter jejuni* PPMQ2b cultures grown at about 37° C.
for about 48 hours in broth media supplemented with various concentrations of organic acids.

| Acid | Acid Concentration (mM) | | | | | |
|---|---|---|---|---|---|---|
| Supplement | 0 | 10 | 20 | 30 | 40 | 50 |
| Lactic | $0.13^{a,w} \pm 0.01$ | $0.12^{a,w} \pm 0.00$ | $0.33^{b,x} \pm 0.02$ | $0.36^{b,x} \pm 0.11$ | $0.31^{b,x} \pm 0.06$ | $0.32^{b,x} \pm 0.07$ |
| Malic | $0.13^{a,w} \pm 0.01$ | $0.15^{a,w} \pm 0.03$ | $0.16^{a,w} \pm 0.05$ | $0.13^{a,w} \pm 0.01$ | $0.33^{b,x} \pm 0.12$ | $0.35^{b,x} \pm 0.02$ |
| Succinic | $0.13^{a,w} \pm 0.01$ | $0.13^{a,w} \pm 0.01$ | $0.12^{a,w} \pm 0.01$ | $0.12^{a,w} \pm 0.01$ | $0.13^{a,w} \pm 0.01$ | $0.16^{a,w} \pm 0.06$ |

[1]Values are averages ± standard deviation. n = 5.
[a-c]Different superscripts indicate significant differences in the absorbance of cultures supplemented with different concentrations of the same acid.
[w-z]Different superscripts indicate significant differences in the absorbance of cultures supplemented with the same concentration of different acid.

TABLE 6

Optical Density[1] of *Campylobacter jejuni* PPMQ3b cultures grown at about 37° C.
for about 48 hours in broth media supplemented with various concentrations of organic acids.

| Acid | Acid Concentrations (mM) | | | | | |
|---|---|---|---|---|---|---|
| Supplement | 0 | 10 | 20 | 30 | 40 | 50 |
| None | $0.10^{a,w} \pm 0.01$ | $0.10^{a,w} \pm 0.01$ | $0.10^{a,w} \pm 0.01$ | $0.10^{a,w} \pm 0.01$ | $0.10^{a,w} \pm 0.01$ | $0.10^{a,w} \pm 0.01$ |
| Citric | $0.10^{a,w} \pm 0.01$ | $0.10^{a,w} \pm 0.01$ | $0.12^{b,w} \pm 0.01$ | $0.11^{ab,w} \pm 0.01$ | $0.11^{ab,w} \pm 0.01$ | $0.11^{ab,w} \pm 0.01$ |
| Fumaric | $0.10^{a,w} \pm 0.01$ | $0.11^{A,W} \pm 0.01$ | $0.21^{B,W} \pm 0.01$ | $0.31^{C,X} \pm 0.05$ | $0.39^{C,X} \pm 0.04$ | $0.34^{C,Y} \pm 0.04$ |
| Lactic | $0.10^{a,w} \pm 0.01$ | $0.14^{ab,w} \pm 0.03$ | $0.21^{b,x} \pm 0.04$ | $0.17^{ab,w} \pm 0.06$ | $0.19^{ab,w} \pm 0.07$ | $0.19^{ab,x} \pm 0.05$ |
| Malic | $0.10^{a,w} \pm 0.01$ | $0.13^{a,w} \pm 0.03$ | $0.32^{b,x} \pm 0.03$ | $0.37^{bc,x} \pm 0.02$ | $0.39^{c,x} \pm 0.03$ | $0.38^{bc,y} \pm 0.04$ |
| Succinic | $0.10^{a,w} \pm 0.01$ | $0.10^{a,w} \pm 0.01$ | $0.13^{a,w} \pm 0.05$ | $0.18^{a,w} \pm 0.08$ | $0.30^{b,x} \pm 0.09$ | $0.34^{b,y} \pm 0.04$ |

[1]Values are averages ± standard deviation. n = 5.
[a-c]Different superscripts indicate significant differences in the absorbance of cultures supplemented with different concentrations of the same acid.
[w-z]Different superscripts indicate significant differences in the absorbance of cultures supplemented with the same concentrations of different acids.

EXAMPLE 3

*Arcobacter* (formerly *Campylobacter*) *butzleri* ATCC 49616, *Campylobacter fetus* subsp. *fetus* ATCC 27374, *Campylobacter coli* ATCC 33559, *Campylobacter jejuni* subsp. *jejuni* ATCC 33560, and *Campylobacter jejuni* subsp. *doylei* ATCC 49349 were obtained from the American Type Culture Collection (ATCC, Manassas, Va. 20110). *A. butzleri* ATCC 49616 was identified as *Campylobacter butzleri* ATCC 49616 in the 18th edition of the ATCC catalog when ordered. However, when the culture arrived it was labeled *Arcobacter* butzleri ATCC 49616. *C. jejuni* PPMQ2b and *C. jejuni* PPMQ3b were prepared as described above in Example 1. All other isolates were from USDA-Agricultural Research Service Russell Research Center, Athens, Ga. Stock cultures of the isolates were maintained by transferring bacteria at weekly intervals to fresh Remel® Blood Agar (Remel, Lenexa, Kans. 66215) and incubating at about 37° C. in a BBL GasPak with a CampyPak Plus Hydrogen+$CO_2$ with Integral Palladium Catalyst for about 48 hours. After incubation the plates were stored at about 4° C.

Basal broth media and a mixture of organic acids were prepared separately. Basal broth media was made by dissolving approximately 20 grams of yeast extract (Difco Laboratories, Detroit, Mich. 48232) and approximately 5 grams of proteose peptone #3 (Difco) in about 900 ml of distilled water. The pH of the solution was adjusted to pH about 7.0 using dilute solutions of NaOH (Spectrum Quality Products, Inc., New Brunswick, N.J. 08901) and HCL (Spectrum Quality Products). The media was dispensed in approximately 9 ml aliquots in screw-capped tubes. An organic acid solution (OA) containing approximately 200 mM each of fumaric (Sigma), DL-lactic (Sigma) DL-malic (Sigma), and succinic (Sigma) acids was prepared by mixing the acids in distilled water that was alkalinated with NaOH pellets to maintain a pH of approximately 11-12 until all acids were dissolved. The final pH of the organic acid solution was adjusted to pH approximately 7.0 with dilute solutions of HCl and NaOH. The basal broth and organic acid mixture were sterilized separately by autoclaving at about 121° C. for about 15 minutes. The basal broth supplemented with the organic acid mixture (BB+OA) was prepared by adding approximately 1 ml of the organic acid solution to approximately 9 ml of basal broth and non-supplemented basal broth (BB) was prepared by adding approximately 1 ml of sterile, distilled water to approximately 9 ml of basal broth. Commercially available media currently recommended for growing Campylobacteriaceae, *Brucella* broth, Mueller-Hinton broth, and fluid thioglycollate medium were prepared according to the manufacturer's instructions, dispensed into test tubes in approximately 10 ml aliquots and sterilized by autoclaving at approximately 121° C. for approximately 15 minutes. The commercially available broth media used in the present study were selected because these media are recommended by the ATCC for culturing *Campylobacter* and *Arcobacter* isolates ordered from their culture collection (Gherna and Pienta (eds.), American Type Culture Collection Catalogue of Bacteria and Bacteriophages, 1992).

Agar media was prepared by dissolving approximately 12 grams of Bacto agar (Difco) into approximately 900 ml of basal broth as described above. A hemin solution was made by mixing approximately 1 gram of hemin chloride, bovine (Sigma) in approximately 2 ml of about 1 M NaOH then raising the total volume of the solution to about 10 ml with distilled water. Approximately 25 milligrams of hemin in solution was added to the agar medium, and the final pH of the medium was adjusted to approximately pH 7.5. Basal agar with and without hemin were autoclaved at about 121° C. for about 15 minutes. Basal agar with organic acids and hemin (BA+OA+hemin) and basal agar with organic acids and no hemin (BA+OA) were prepared by adding approximately 100 ml of a sterile 200 mM organic acid mixture (pH about 7.0) to approximately 900 ml of agar medium with hemin or approximately 900 ml agar medium without hemin.

Stock cultures of Campylobacter spp. and A. butzleri were streaked onto Remel® Blood Agar plates and incubated as described above in Example 1. The cultures were harvested by adding about 9 ml of an about 0.1% Bacto Peptone solution to the surface of the plates and using sterile bacterial cell spreaders to scrape cell growth from the plates. Harvested bacterial suspensions for each of the isolates contained approximately $10^9$ colony-forming units (CFU)/ml. Growth of the bacteria in broth media was examined by adding approximately 9.1 ml of the bacterial suspension to approximately 10 ml of BB, BB+OA, brucella broth, Mueller-Hinton Broth, and fluid thioglycollate medium. Test tubes containing the inoculated media were transferred to a MACS VA500 Microaerophilic Workstation (Don Whitley Scientific Limited, West Yorkshire, England) filled with an atmosphere of about 82% nitrogen, 10% oxygen, and 8% carbon dioxide. Honeycomb 2 cuvette plates (Labsystems, Inc., Franklin, Mass. 02038) were placed in the chamber and about 0.1 ml of each inoculated medium was transferred to the wells of the cuvette plates. The cell suspensions were overlaid with about 0.1 ml of sterilized, heavy, white mineral oil (Sigma) and the filled Honeycomb 2 plates were removed from the microaerophilic chamber and placed in the incubator tray of a Bioscreen C Microbiology Reader (Thermo Electron Corp., West Palm Beach, Fla. 33407) that was operated by a computer running Growth Curves Software v. 2.28 (Transgalactic Ltd., Helsinki, Finland). Cultures were incubated in the Microbiology reader at about 37° C. for approximately 48 hours and absorbance of the cultures was measured at about 30 minute intervals with the wide band (420-580 nm) filter. Each experiment was replicated 5 times.

To compare the growth of the isolates on the commercially available blood agar media (Remel), cultures were harvested from Remel® Blood Agar plates and serial dilutions of the cultures were spread plated onto BA+OA, BA+OA+hemin, and Remel® Blood Agar plates. Plates were transferred into the MACS VA500 Microaerophilic Workstation and incubated at about 37° C. for about 48 hours. The colony-forming units were counted after incubation. Each experiment was replicated three times.

For statistical analysis, group means of culture absorbances were compared to determine significant differences in the turbidity of bacterial cultures grown in different media. Data were analyzed as in Example 2.

In the broth media, growth of most of the Campylobacteriaceae was significantly better in BB+OA than in BB, brucella broth, Mueller-Hinton broth, or fluid thioglycollate medium (Table 7). After about 48 hours, the absorbance of cultures of A. butzleri and of 10 of the 15 of the Campylobacter isolates grown in BB+OA was significantly higher than cultures grown in BB, brucella broth, Mueller-Hinton broth, or fluid thioglycollate medium. Although there was no significant difference in the absorbance of cultures of C. jejuni PPMQ3b and C. jejuni AMRU 63915 grown in BB+OA or brucella broth, the absorbance of cultures grown in these two media were significantly higher than the absorbance of cultures grown in the other 3 media. Likewise, there was no significant difference in the absorbance of cultures of C. jejuni AMRU 86119 grown in BB or BB+OA, but the absorbance of cultures grown in the these media were significantly higher than the absorbance of isolates grown in the other three media. Furthermore, although there was no difference in the absorbance of cultures of C. jejuni AMRU 199708 grown in BB+OA or Mueller-Hinton broth, the absorbance of cultures grown in these media were significantly higher than the absorbance of cultures grown in brucella broth or fluid thioglycollate medium. Similarly, the absorbance of cultures of C. jejuni AMRU 48100 cultures grown in BB, BB+OA or brucella broth was significantly higher than the absorbance of cultures grown in Mueller-Hinton broth or fluid thioglycollate medium. Finally, the absorbance of C. jejuni AMRU 67-8 cultures grown in fluid thioglycollate medium was significantly lower than in cultures grown in either of the other media. Findings indicate that the BB+OA medium can support the growth of A. butzleri, C. jejuni, and C. coli significantly better than or as well as the commercially available media used in the present study. Yeast extract and proteose peptone in the basal medium served as a source of amino acids, vitamins, and other growth factors (Difco Manual, Tenth Edition, Difco Laboratories, Inc., Detroit, Mich., 1984) that can support the growth of Campylobacteriaceae. The organic acid solution supplement provided an additional energy source that apparently stimulated the growth of the bacteria. Since Campylobacteriaceae can produce energy by oxidizing some intermediates of the TCA cycle (Stern and Line, Campylobacter, In: Lund et al (eds) The Microbiological Safety and Quality of Food, Aspen Publishers, Gaithersburg, Md., Volume II, 1040-1056, 2000), the increased growth of the bacteria in BB+OA was probably due to the metabolism of fumaric, malic, and succinic acids by the bacteria. Other research has shown that the metabolic activity of the intestinal anaerobe, Veillonella, is stimulated when the bacterium is provided a mixture of succinic and lactic acid (Hinton and Hume, Avian Dis., Volume 39, 309-316, 1995). Findings from the present study indicated that the growth of Campylobacter was greatest when media was supplemented with a mixture containing all four organic acids than when the media was supplemented with only one organic acid (Table 7).

On agar media, there was no significant difference in the number of CFU/ml recovered from any of the Campylobacter cultures plated on BA+OA+hemin or Remel® Blood Agar (Table 8). Also, there was no significant difference in the number of C. jejuni PPMQ2b recovered on BA+OA without hemin, BA+OA+hemin, or Remel® Blood Agar; however, for all other isolates, significantly fewer bacteria were recovered on BA without hemin than on the other two agar media. Blood and hemin are used alone and in combination in some Campylobacter and Arcobacter media as nutritional supplements and oxygen scavengers. Results from the present example indicate that adding only hemin to the novel medium increased recovery of Campylobacteriaceae to levels that are not significantly different from recovery levels on media supplemented with blood. Therefore, the bacteria were able to grow as well on the chemically defined, blood-free media of the present invention than on commercially available, blood-supplemented media.

TABLE 7

Absorbance[1] of *Arcobacter butzleri* and *Campylobacter* spp. grown at about 37° C. for about 48 hours in broth media.

| Isolate | Basal Broth (BB) | Basal Broth + OA[2] | Brucella Agar | Mueller-Hinton Broth | Fluid Thioglycollate medium |
|---|---|---|---|---|---|
| *A. butzleri* ATCC 49616 | $0.44^c \pm 0.02$ | $0.49^d \pm 0.03$ | $0.20^b \pm 0.01$ | $0.12^a \pm 0.02$ | $0.17^b \pm 0.01$ |
| *C. jejuni* PPMQ2b | $0.38^c \pm 0.02$ | $0.47^d \pm 0.02$ | $0.33^c \pm 0.06$ | $0.27^b \pm 0.03$ | $0.16^a \pm 0.01$ |
| *C. jejuni* PPMQ3b | $0.33^c \pm 0.04$ | $0.49^d \pm 0.04$ | $0.44^d \pm 0.02$ | $0.26^b \pm 0.03$ | $0.17^a \pm 0.01$ |
| *C. jejuni* AMRU 67-8 | $0.41^b \pm 0.04$ | $0.52^b \pm 0.02$ | $0.46^b \pm 0.10$ | $0.48^b \pm 0.11$ | $0.24^a \pm 0.02$ |
| *C. jejuni* AMRU 111-3 | $0.34^b \pm 0.12$ | $0.61^c \pm 0.09$ | $0.36^b \pm 0.06$ | $0.40^b \pm 0.05$ | $0.17^a \pm 0.02$ |
| *C. jejuni* AMRU 127-2 | $0.12^a \pm 0.01$ | $0.66^c \pm 0.18$ | $0.38^b \pm 0.13$ | $0.37^b \pm 0.05$ | $0.27^{ab} \pm 0.03$ |
| *C. jejuni* AMRU 129-25 | $0.37^a \pm 0.02$ | $0.68^b \pm 0.12$ | $0.48^a \pm 0.06$ | $0.45^a \pm 0.09$ | $0.36^a \pm 0.05$ |
| *C. jejuni* AMRU 144-3 | $0.48^b \pm 0.01$ | $0.66^b \pm 0.05$ | $0.50^b \pm 0.02$ | $0.49^b \pm 0.07$ | $0.29^a \pm 0.03$ |
| *C. fetus* subsp. *fetus* ATCC 27349 | $0.29^b \pm 0.01$ | $0.73^e \pm 0.01$ | $0.38^c \pm 0.01$ | $0.42^d \pm 0.02$ | $0.19^a \pm 0.01$ |
| *C. jejuni* AMRU 1997-8 | $0.56^c \pm 0.05$ | $0.56^c \pm 0.02$ | $0.45^b \pm 0.03$ | $0.60^c \pm 0.01$ | $0.17^a \pm 0.01$ |
| *C. coli* ATCC 33559 | $0.26^{ab} \pm 0.02$ | $0.53^d \pm 0.06$ | $0.31^b \pm 0.02$ | $0.44^c \pm 0.06$ | $0.23^a \pm 0.02$ |
| *C. jejuni* ATCC 33560 | $0.10^a \pm 0.02$ | $0.50^d \pm 0.03$ | $0.15^c \pm 0.02$ | $0.13^{b,c} \pm 0.02$ | $0.08^a \pm 0.03$ |
| *C. jejuni* AMRU 48100 | $0.42^c \pm 0.02$ | $0.48^c \pm 0.02$ | $0.41^c \pm 0.08$ | $0.31^b \pm 0.06$ | $0.17^b \pm 0.02$ |
| *C. jejuni* AMRU 63915 | $0.30^a \pm 0.09$ | $0.54^b \pm 0.07$ | $0.36^b \pm 0.06$ | $0.41^a \pm 0.08$ | $0.09^a \pm 0.01$ |
| *C. jejuni* AMRU 86005 | $0.21^{ab} \pm 0.05$ | $0.55^c \pm 0.13$ | $0.24^b \pm 0.05$ | $0.09^a \pm 0.05$ | $0.11^{ab} \pm 0.04$ |
| *C. jejuni* AMRU 86119 | $0.70^c \pm 0.06$ | $0.69^c \pm 0.06$ | $0.47^b \pm 0.04$ | $0.54^b \pm 0.08$ | $0.27^a \pm 0.04$ |

[1]Values are averages ± standard deviation, n = 5.
[2]Media supplemented with organic acid mixture of 20 mM fumaric, lactic, malic, and succinic acids.
[a-e]Within rows, different superscripts indicate significant differences in the OD of cultures grown in different media.

TABLE 8

Average colony-forming units/ml of *Arcobacter* and *Campylobacter* spp. recovered on Remel ® Blood Agar, Basal Agar + OA[2], and Basal Agar + OA + Hemin[3] incubated at about 37° C. for about 48 hours.

| Isolate | Log CFU/ml | | |
|---|---|---|---|
| | Blood Agar | Basal Agar + OA | Basal Agar + OA + Hemin |
| *A. butzleri* ATCC49616 | $9.03^b \pm 0.23$ | $6.74^a \pm 0.30$ | $9.04^b \pm 0.04$ |
| *C. jejuni* PPMQ2b | $9.61^a \pm 0.13$ | $9.45^a \pm 0.06$ | $9.62^a \pm 0.01$ |
| *C. jejuni* PPMQ3b | $9.71^b \pm 0.18$ | $8.99^a \pm 0.35$ | $9.79^b \pm 0.05$ |
| *C. jejuni* AMRU 67-8 | $9.94^b \pm 0.05$ | $6.07^a \pm 0.32$ | $9.55^b \pm 0.52$ |
| *C. jejuni* AMRU 111-3 | $9.64^b \pm 0.11$ | $9.07^a \pm 0.05$ | $9.45^b \pm 0.11$ |
| *C. jejuni* ANRU 127-2 | $9.83^b \pm 0.09$ | $9.45^a \pm 0.04$ | $9.81^b \pm 0.10$ |
| *C. jejuni* AMRU129-25 | $9.71^b \pm 0.20$ | $9.43^a \pm 0.15$ | $9.62^b \pm 0.08$ |
| *C. jejuni* AMRU 144-3 | $9.99^b \pm 0.06$ | $8.73^a \pm 0.73$ | $9.73^{ab} \pm 0.17$ |
| *C. fetus* subsp. *fetus* ATCC 27349 | $9.40^b \pm 0.25$ | $7.58^a \pm 0.24$ | $9.59^b \pm 0.07$ |
| *C. jejuni* AMRU1997-8 | $9.69^b \pm 0.10$ | $8.70^a \pm 0.19$ | $9.60^b \pm 0.08$ |
| *C. coli* ATCC 33559 | $9.47^b \pm 0.07$ | $7.67^a \pm 0.27$ | $9.46^b \pm 0.06$ |
| *C. jejuni* ATCC 33560 | $8.97^b \pm 0.11$ | $7.83^a \pm 0.32$ | $8.84^b \pm 0.06$ |
| *C. jejuni* AMRU 48100 | $9.64^b \pm 0.10$ | $7.92^a \pm 0.69$ | $9.54^b \pm 0.11$ |
| *C. jejuni* subsp. *doylei* ATCC 49349 | $9.45^b \pm 0.08$ | $8.61^a \pm 0.22$ | $9.22^b \pm 0.10$ |

TABLE 8-continued

Average colony-forming units/ml of *Arcobacter* and *Campylobacter* spp. recovered on Remel ® Blood Agar, Basal Agar + OA[2], and Basal Agar + OA + Hemin[3] incubated at about 37° C. for about 48 hours.

| Isolate | Log CFU/ml | | |
|---|---|---|---|
| | Blood Agar | Basal Agar + OA | Basal Agar + OA + Hemin |
| *C. jejuni* AMRU 86005 | $9.39^b \pm 0.19$ | $7.29^a \pm 0.33$ | $9.30^b \pm 0.13$ |
| *C. jejuni* AMRU 86119 | $9.65^b \pm 0.10$ | $8.54^a \pm 0.36$ | $9.49^b \pm 0.15$ |

[1]Values are averages ± standard deviation. n = 3.
[2]Media supplemented with organic acid mixture of about 20 mN fumaric, lactic, malic, and succinic acids.
[3]Media supplemented with organic acid mixture and about 25 mg/l hemin.
[a-e]Within rows, different superscripts indicate significant differences in the OD of cultures grown in different media.

The foregoing detailed description is for the purpose of illustration. Such detail is solely for that purpose and those skilled in the art can make variations therein without departing from the spirit and scope of the invention.

I claim:

1. A chemically defined composition consisting of:
   (a) an oxygen scavenger,
   (b) a yeast extract in a range of approximately 0.5% to approximately 2.0%,
   (c) an energy source consisting of a composition of fumaric acid, malic acid, DL-lactic acid and succinic acid in amounts in the range of approximately 10 mM to approximately 40 mM; and
   (d) an amino acid source selected from the group consisting of peptone, tryptone, tryptose, soytone, and beef extract in a range of about 0.5% to about 2.0%; wherein said chemically defined composition supports the in vitro growth of *Campylobacter* and *Arcobacter* species.

* * * * *